United States Patent
Roché

[11] Patent Number: 5,972,858
[45] Date of Patent: Oct. 26, 1999

[54] GREASE CUTTING COMPOSITION

[76] Inventor: Joseph M. Roché, 1915 Casa Dr., Arnold, Mo. 63010

[21] Appl. No.: 09/025,487

[22] Filed: Feb. 18, 1998

[51] Int. Cl.$^6$ .............. A61K 7/50; A61K 7/48; C11D 17/00; C11D 3/38

[52] U.S. Cl. .......... 510/137; 510/157; 510/158; 510/159; 510/365; 510/403; 510/463

[58] Field of Search ................. 510/130, 137, 510/157, 158, 159, 365, 403, 463

[56] References Cited

U.S. PATENT DOCUMENTS

| | | | |
|---|---|---|---|
| 4,256,600 | 3/1981 | Lewiset | 252/132 |
| 5,338,541 | 8/1994 | Matz et al. | 424/71 |
| 5,364,879 | 11/1994 | Herman | 514/452 |
| 5,464,554 | 11/1995 | Gu et al. | 252/121 |
| 5,614,484 | 3/1997 | Panadiker | 510/102 |
| 5,658,584 | 8/1997 | Yamaguchi | 424/405 |
| 5,705,465 | 1/1998 | Angevaare et al. | 510/220 |

*Primary Examiner*—Necholus Ogden
*Attorney, Agent, or Firm*—Edward H. Renner

[57] ABSTRACT

A grease cutting soap based cleaning composition, for hand cleaning for example, has the following composition by weight:

| Ingredients | Per Cent by Weight |
|---|---|
| Sodium salt fatty acid soap | 20–25 |
| Hydrogen peroxide solution (3%) | 8–12 |
| Glycerin | 5–10 |
| Cocoa butter | 4–7 |
| Citronella oil | .05–1 |
| Water | to balance |
| | 100% |

The composition exhibits superior grease cutting and cleaning properties, with or without the use of additional water. The composition is mild and non-irritating to the skin.

6 Claims, No Drawings

GREASE CUTTING COMPOSITION

BACKGROUND OF THE INVENTION

This invention pertains to semi-liquid soap based hand cleaners and degreasers. In a more particular aspect, the invention provides a semi-liquid hand cleaner and degreaser so modified that, considering the fact that it contains soap, and not a synthetic detergent, it has unexpected grease and oil cutting properties.

I am aware of the following U.S. patents, the disclosures of which are incorporated by reference herein:

U.S. Pat. No. 5,338,541
U.S. Pat. No. 5,364,879
U.S. Pat. No. 5,658,584

SUMMARY OF THE INVENTION

The word "soap" is the technical term for alkali and alkaline earth metal salts of long chain fatty acids, for instance, a lauric-stearic acid mixture. However, the common use of the term is for the sodium or potassium salts, which are water soluble and have use as cleaning agents. The fatty acids are commonly derived from fatty oils such as triglycerides. The long chain fatty acids in soaps are generally aliphatic acids having ten to eighteen carbon atoms. Examples of such acids are stearic acid, lauric acid, myristic acid, palmitic acid, and the like. Usually they are derived from such fats as beef tallow and lard, and such vegetable oils as corn, coconut, olive, palm, soybean and peanut oils. Normally the acids are saturated although unsaturated fatty acids such as oleic acid are present in fats and oils and hence have been used in soap manufacture.

Cleaning compositions which are not soaps are the synthetic detergents, such as sodium lauryl sulfate. Detergents are synthesized, for example, by treating a long chain alcohol with sulfuric acid and sodium hydroxide.

It is known that an advantage of synthetic detergents is that detergents overcome the hard water problem. Hard water contains calcium and magnesium salts which react with soluble soaps to form insoluble calcium and magnesium soaps, forming the ring in the bathtub, or leaving a residue in clothes being washed. Less known is the fact that soaps do not remove grease as well as detergent containing laundry compositions, and, dish washing compositions, which are formulated to cleanse greasy objects.

However, synthetic detergents are too harsh for use as hand cleaners, that is, body and hand soaps, but they do have a high solvency for oil and grease. Detergents are less desirable than soaps since many have been found not biodegradable. Nevertheless such detergents are in use for dish and clothes washing because of their ability to remove grease. It is this grease-cutting action with which this invention is concerned. It is important to modify a soap based composition to render it more effective in emulsifying and dissolving grease and oils.

In simple terms, the action of a soap or detergent involves a polar end and a non-polar end of the soap molecule. The polar end is water-soluble, and the non-polar end is oil-soluble. The cleansing action of a soap thus is an extremely complicated matter. For this reason the problem of the ineffectiveness of soap against grease has not been entirely solved. As an example, in the preparation of toilet soaps steps are taken to ensure that just the right amount of sodium hydroxide is used to react with the fatty acid; these soaps are substantially pH neutral. If a soap is formulated to be effective against grease it usually contains an excess of sodium hydroxide which helps in removing the grease. A soap so formulated is pH basic and is harsh on human skin and is undesirable for use as a personal cleaning composition. This invention produces a soap based cleaning composition which is substantially pH neutral yet which cuts grease and oils better than known soaps. The composition of the invention is gentle enough for use on the hands and body as a personal cleaning composition and degreaser. Moreover, this result is achieved without the use mechanical abrasives, such as pumice.

It has been found that the incorporation of hydrogen peroxide with soap renders the soap effective against grease while retaining the other desirable characteristics of the soap. Accordingly, a cleaning composition is provided herein having a grease cutting action superior to that of conventional soaps. The soap is in liquid form or semi-liquid form and includes an alkali metal salt of a fatty acid, and 40 to 50 percent hydrogen peroxide by weight based on the fatty acid and sufficient water to render the soap dispensable. Further, it has been found that incorporation of glycerin and oil of citronella contribute to the degreasing properties of the cleaning composition.

It is an object of this invention to provide a grease removing cleaning composition which does not contain harsh solvents and detergents.

It is an object of this invention to provide a grease removing cleaning composition which does not require mechanical abrasives, such as pumice.

It is an object of this invention to provide a soap-based cleaning composition which is highly effective at removing grease and oils.

It is an object of this invention to provide a soap based cleaning composition which is effective without the use of additional water.

It is an object of this invention to provide a semi-liquid soap based cleaning composition which is effective as a grease cutting hand cleaner.

It is an object of this invention to provide a semi-liquid soap based cleaning composition containing hydrogen peroxide.

It is an object of this invention to provide a soap based cleaning composition containing hydrogen peroxide, oil of citronella and glycerin, in combination.

These and other objects of the invention will be apparent from the following Description of the Preferred Embodiments and included examples.

DESCRIPTION OF THE PREFERRED EMBODIMENTS

Diperoxide compounds have been used for medicinal purposes, and, as disclosed in U.S. Pat. No. 5,364,879, they are included in a suitable pharmacological soap for treatment of bacterial, viral, protozoal and fungal infections. However, I am not aware of the incorporation of hydrogen peroxide in a soap, particularly for its effectiveness against grease. In addition, in my preferred embodiment of the invention, the cleaning composition includes an essential oil, a moistening agent and citronella oil. In U.S. Pat. No. 5,338,541 the essential oil, cocoa butter, is suggested for sun screens, and the moistening agent, glycerin, is disclosed in a shaving cream. Citronellic acid is disclosed in an antimicrobial soap in U.S. Pat. No. 5,658584, but citronella oil is not suggested. Their use in my composition in combination with the hydrogen peroxide, may be synergistic. If it is not, it at least renders the composition less harsh and in combination with glycerin leaves the skin soft. This preferred embodiment will now be described in more detail in specific examples.

EXAMPLE 1

In order to utilize the action of the hydrogen peroxide, the soap herein is a water-based semi-liquid. The ingredients are in a selected weight percentage range, with the remainder being water in an amount bringing the total percentage to one hundred. The ingredients making up my liquid composition are the following within the ranges shown.

| Ingredient | Weight Per Cent |
|---|---|
| Sodium salt of a fatty acid | 20 to 25 |
| Hydrogen peroxide (3%) | 8 to 12 |
| Glycerin | 5 to 10 |
| Cocoa butter | 4 to 7 |
| Citronella oil | 0.5 to 1 |
| Water | Remainder to 100% |

Within these ranges, my preferred composition can be illustrated and a suitable cleaning composition could be made, as follows:

| Ingredient | Weight Per Cent |
|---|---|
| Sodium Laurate | 20.7 |
| Hydrogen Peroxide (3%) | 9.3 |
| Glycerin | 6.9 |
| Cocoa Buffer | 4.7 |
| Citronella Oil | 0.8 |
| Water | 57.6 |
| | 100.0 |

EXAMPLE 2

As a specific example, a cleaning composition was made as follows:

| Ingredients | |
|---|---|
| White Soap (Ivory ®) | 36.0 oz |
| Hydrogen peroxide (3%) | 16.0 oz |
| Cocoa butter | 8.0 oz |
| Glycerin | 12.0 oz |
| Oil of citronella | 1.5 oz |
| Water | 100.0 oz |

Procedure

The soap and cocoa butter are solids and were pulverized, and then mixed. To the powdered mixture of soap and cocoa butter, the hydrogen peroxide, citronella oil, glycerin and water were added. The mixture was heated to a temperature just high enough to dissolve and melt the powder mix, and only long enough to liquify the solids. In other words, the mixture was not cooked, but heated only sufficiently to form a mix. After the mix was formed, the heat was removed and the mix was transferred to a blender. Here the mix was blended to form the desired emulsified product. The emulsion became stable when the blending proceeded until a good foam formed on top of the mix. If desired, a coloring agent, such as a food grade color, could have been added during the emulsification step. Additional perfumes and additives could also have been added at this step. The mix was then agitated slowly during the cooling period to form the final product. Until it cooled the soap appeared very thin, but it set up well, forming a stable semi-liquid emulsion when it cooled.

Testing

Samples of the semi-liquid composition were tested by mechanics for removing grease from hands, by printers for removing printing ink from hands and by various other technicians. The mechanics were unanimous in reporting that conventional soaps did not work well at removing automotive grease, for example, whereas the composition of the invention removed grease from their hands and unexpectedly could be used as a waterless cleaner. The printers reported excellent results with the composition in removing printing inks, including oil based colored inks. All reported that the composition is effective in getting into the pores, creases and wrinkles in hands and arms and removed entrapped grease and grime. All of the groups reported that the composition left hands soft and clean without skin irritation even on repeated use. However, the composition exhibits a slight bleaching action on hair and may not be suitable for all uses as a shampoo.

It can be seen that the cleaning composition of the invention resembles detergents in effectiveness. It cleans greasy hands, arms, and the body when grease removal is a consideration, whereas conventional soaps do not. It is unexpectedly superior to commercial hand and body soaps. Various colors can be added to the composition. Perfumes, preservatives, lanolin and other additives commonly added to toilet soaps can also be added. Such additions and modifications are deemed to be within the scope of this invention.

It will be appreciated by those skilled in the art that various modifications and changes can be made to the specific embodiments disclosed herein without departing from the spirit of the invention. The examples given herein are illustrative and not for pusposes of limitation. It is intended that the invention is to be limited only by the claims appended hereto and by their equivalents.

I claim:

1. A semi-liquid soap based cleaning composition being substantially pH neutral and non-irritating and non-abrasive to skin, the composition having an effective grease cutting action and being effective at removing grease and oil, the composition consisting essentially of:

| Ingredients | Weight per cent |
|---|---|
| Sodium soap | About 21 |
| Hydrogen peroxide (3%) | About 10 |
| Glycerin | About 7 |
| Cocoa butter | About 5 |
| Citronella oil | About 1 |
| Water | to balance |
| | 100 |

2. The cleaning composition of claim 1 wherein the sodium soap is a sodium salt of a fatty acid.

3. The cleaning composition of claim 2 wherein the sodium salt is the sodium salt of a mixture of fatty acids derived from a vegetable oil.

4. The cleaning composition of claim 3 wherein at least some of the fatty acids are derived from animal fats.

5. The cleaning composition of claim 1 wherein the composition contains perfumes.

6. The cleaning composition of claim 2 wherein the sodium salt is sodium laurate.

* * * * *